(12) United States Patent
Hada et al.

(10) Patent No.: US 6,578,563 B2
(45) Date of Patent: Jun. 17, 2003

(54) POWER SUPPLY CONTROL SYSTEM FOR HEATER USED IN GAS SENSOR

(75) Inventors: Satoshi Hada, Inazawa (JP); Eiichi Kurokawa, Okazaki (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 10/202,865

(22) Filed: Jul. 26, 2002

(65) Prior Publication Data

US 2003/0019486 A1 Jan. 30, 2003

(30) Foreign Application Priority Data

Jul. 27, 2001 (JP) ..................... 2001-227684
Jun. 10, 2002 (JP) ..................... 2002-169060

(51) Int. Cl.⁷ ............................ F02D 41/00
(52) U.S. Cl. ..................... 123/697; 204/425
(58) Field of Search ................ 123/697, 434, 123/694, 693; 204/425, 424

(56) References Cited

U.S. PATENT DOCUMENTS 5,787,866 A    8/1998  Sugiyama et al.
6,136,170 A  * 10/2000  Inoue et al. ............. 204/424

FOREIGN PATENT DOCUMENTS

JP    9-281075    10/1997
JP    11-83795     3/1999

* cited by examiner

Primary Examiner—Bibhu Mohanty
(74) Attorney, Agent, or Firm—Nixon & Vanderhye P.C.

(57) ABSTRACT

A heater power supply control system is provided for controlling the temperature of a heater used to heat a solid electrolyte-made sensor element of a gas concentration sensor up to a desired activation temperature. The heater power supply control system measures a resistance value of the sensor element and controls an electric power supply to the heater using a PI control function. The heater power supply control system works to limit the value of an integral term of the PI control function in the course of activation of the sensor element, thereby avoiding overshoot of the resistance value of the sensor element, which avoids thermal damage of the sensor element.

18 Claims, 11 Drawing Sheets

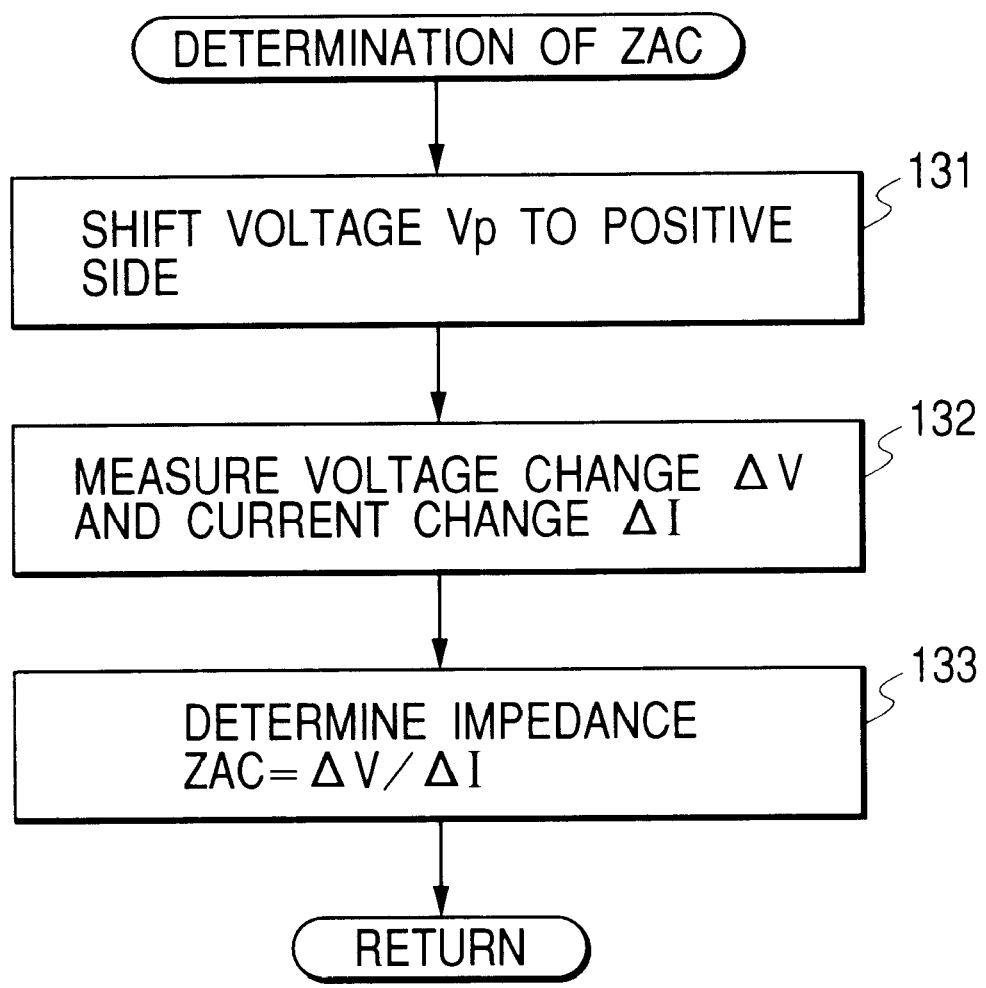

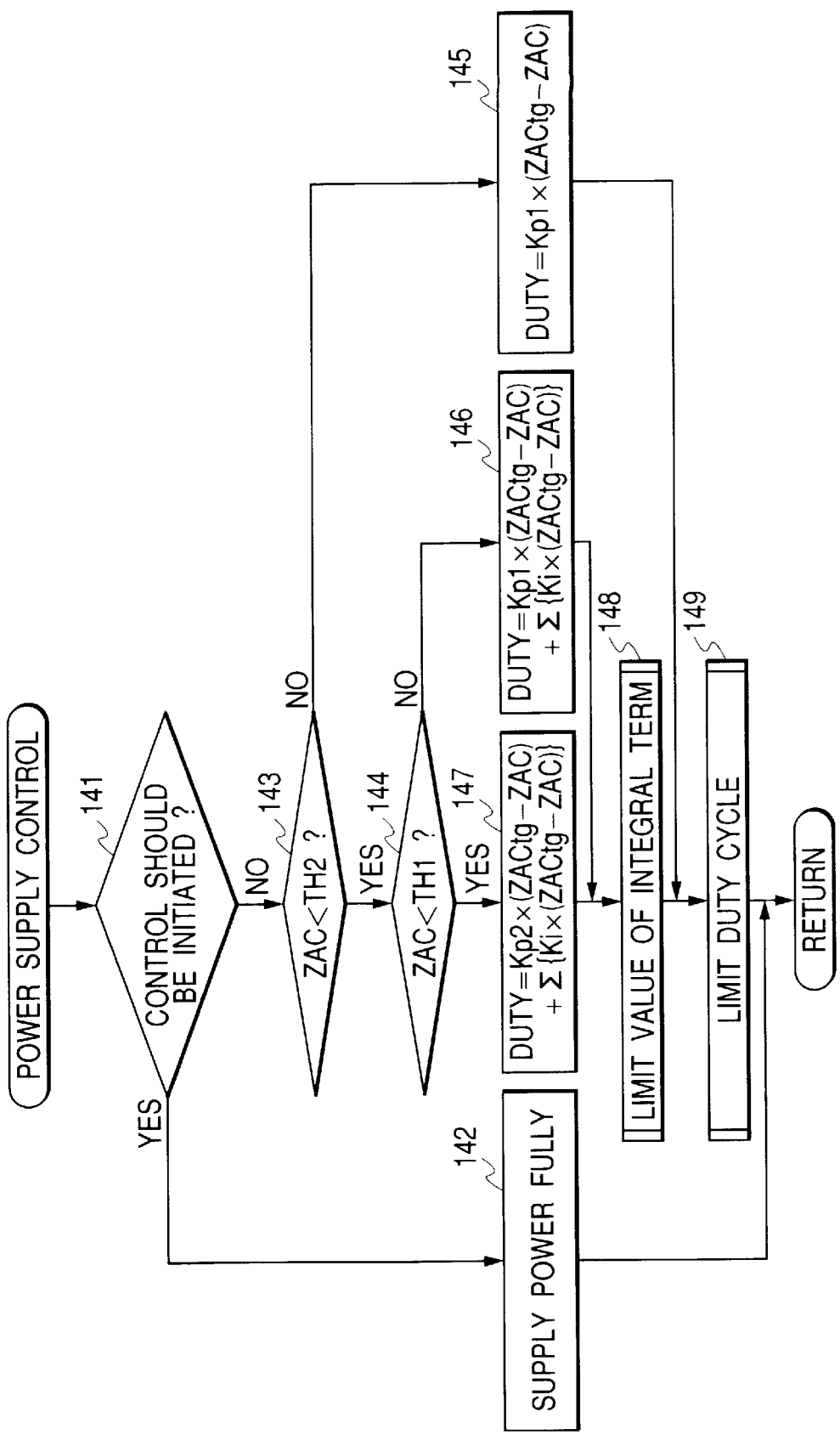

POWER SUPPLY CONTROL SYSTEM FOR HEATER USED IN GAS SENSOR

BACKGROUND OF THE INVENTION

1. Technical Field of the Invention

The present invention relates generally to a power supply control system for a heater working to heat a gas sensor such as a gas concentration sensor up to a desired activation temperature which may be employed in an air-fuel ratio control system for automotive vehicles for measuring the concentration of a specified gas component such as $O_2$, NOx, or CO contained in exhaust emissions from the engine.

2. Background Art

Air-fuel ratio control for automotive internal combustion engines is typically accomplished using an output of a gas concentration sensor. Such a gas concentration sensor has a sensor element which includes a solid electrolyte member made of zirconia. The sensor element works to measure the concentration of a given gas component (e.g., oxygen) of exhaust gasses of the engine. An air-fuel ratio control system determines an air-fuel ratio as a function of the measured concentration of the gas component. Ensuring the accuracy of such a determination requires keeping the sensor element at a desired activation temperature. This is usually achieved using a heater embedded in the sensor element. The amount of heat generated by the heater is regulated, for example, by changing the duty cycle of a pulse signal used to switching on and off a power supply to the heater. A feedback control system is proposed which measures the resistance of the sensor element and achieves the regulation of the power supply by changing the duty cycle of the pulse signal to bring the measured resistance to agreement with a target one.

A heater power supply control system is known which supplies the power to the heater fully (i.e., the duty cycle= 100%) at the startup of the engine, after which a power supply to the heater is changed in feedback control as a function of a difference between an actually measured resistance of the sensor element and a target one. The feedback control is implemented by, for example, the so-called PI control using proportional and integral gains. In the course of activation of the sensor element, that is, during a rise in temperature of the sensor element, a difference between the resistance of the sensor element and the target value is great, so that the integral gain increases gradually. This results in an excessive increase in integral gain when the resistance of the sensor element reaches the target value, which leads to overshoot of the resistance of the sensor element. The occurrence of such an overshoot results in an excessive rise in temperature of the sensor element, which may cause damage to the sensor element.

A rapid change in ambient temperature of the sensor element after the sensor element is activated completely will result in a delay in the feedback control, thus leading to overheating of the sensor element.

SUMMARY OF THE INVENTION

It is therefore a principal object of the present invention to avoid the disadvantages of the prior art.

It is another object of the present invention to provide a heater control system for gas concentration sensors which is designed to avoid overheating of a sensor element, thereby protecting the sensor element against thermal breakage.

According to one aspect of the invention, there is provided a heater control apparatus for controlling a temperature of a heater used to heat a solid electrolyte-made sensor element of a gas concentration sensor up to a temperature at which the sensor element is activated to provide a correct gas concentration output. The heater control apparatus comprises: (a) a control circuit working to control a power supply to the heater up to a desired activation temperature; (b) a sensor element resistance determining circuit working to determine a resistance value of the sensor element of the gas concentration sensor; and (c) a heater control variable determining circuit determining a heater control variable for controlling the power supply to the heater in the control circuit based on a value of an integral term in a control function which is determined as a function of a difference between the resistance value determined by the sensor element resistance determining circuit and a target value. The heater control variable determining circuit puts a limitation on increasing of the value of the integral term until the resistance value of the sensor element reaches a preselected value in the course of activation of the sensor element. If the integral gain is increased excessively in the course of heating of the sensor element from a cold state thereof, it may cause the resistance value of the sensor element to overshoot the target value, thereby resulting in an excess increase in temperature of the sensor element, leading to thermal breakage thereof. The heater control apparatus works to limit the increasing of the value of the integral term during the activation of the sensor element for avoiding such a problem.

In the preferred mode of the invention, the heater control variable determining circuit sets the value of the integral term to zero until the resistance value of the sensor element reaches the preselected value.

The heater control variable determining circuit may determine the heater control variable only using a value of a proportional term in the control function defined in proportional plus integral control until the resistance value of the sensor element reaches the preselected value in the course of activation of the sensor element, after which the heater control variable determining circuit determines the heater control variable using both the proportional term and the integral term.

The heater control variable determining circuit may set the value of the integral term to a value defined near zero until the resistance value of the sensor element reaches the preselected value.

The heater control variable determining circuit may reset the value of the integral term when the resistance value of the sensor element reaches the preselected value during the activation of the sensor element.

The heater control variable determining circuit may work to limit a maximum value of the integral term to a preselected guard value.

The heater control variable determining circuit determines the heater control variable so as to supply power to the heater substantially fully at a given initial stage of increasing temperature of the heater and subsequently determines the heater control variable using the control function.

The heater control variable determining circuit may increase at least one of gains of the integral term and a proportional term in the control function defined in proportional plus integral control when the resistance value of the sensor element is shifted to a side on which temperature of the sensor element is increased out of a controlled range defined across the target value.

The heater control variable determining circuit may alternatively increase at least one of the gains of the integral term and the proportional term based on a temperature-resistance characteristic of the sensor element within a feedback controlled range in which the power supply to the heater is controlled as a function of the difference between the resistance value determined by the sensor element resistance determining circuit and the target value.

The gas concentration sensor may be employed to sense an exhaust gas of an automotive engine.

According to the second aspect of the invention, there is provided a heater control apparatus which comprises: (a) a control circuit working to control a power supply to a heater used to heat a solid electrolyte-made sensor element of a gas concentration sensor up to a temperature at which the sensor element is activated to provide a desired gas concentration output; (b) a sensor element resistance determining circuit working to determine a resistance value of the sensor element of the gas concentration sensor; and (c) a heater control variable determining circuit determining a heater control variable for controlling the power supply to the heater in the control circuit based on values of an integral and a proportional term of a control function used in proportional plug integral control which are each determined as a function of a difference between the resistance value determined by the sensor element resistance determining circuit and a target value. The heater control variable determining circuit increases at least one of gains of the integral and proportional terms when the resistance value of the sensor element is shifted to a side on which temperature of the sensor element is increased out of a controlled range defined across the target value.

In the preferred mode of the invention, the heater control variable determining circuit increases at least one of the gains of the integral and proportional terms based on a temperature-resistance characteristic of the sensor element within a feedback controlled range in which the power supply to the heater is controlled as a function of the difference between the resistance value determined by the sensor element resistance determining circuit and the target value.

The gas concentration sensor may be employed to sense an exhaust gas of an automotive engine.

According to the third aspect of the invention, there is provided a heater control apparatus which comprises: (a) a control circuit working to control a power supply to a heater used to heat a solid electrolyte-made sensor element of a gas concentration sensor up to a temperature at which the sensor element is activated to provide a desired gas concentration output; (b) a sensor element resistance determining circuit working to determine a resistance value of the sensor element of the gas concentration sensor; and (c) a heater control variable determining circuit determining a heater control variable for controlling the power supply to the heater in the control circuit as a function of a difference between the resistance value determined by the sensor element resistance determining circuit and a target value so as to bring the difference into agreement with the target value. The heater control variable determining circuit switches the target value between an initial value and a final value lower than the initial value during activation of the sensor element.

In the preferred mode of the invention, the heater control variable determining circuit switches the target value from the initial value to the final value when the target value has first overshot the initial value and reached the initial value again.

The heater control variable determining circuit may alternatively switch the target value from the initial value to the final value after an elapse of a preselected period of time from when the target value reaches the initial value.

The initial value may be defined within a range of the final value plus 10Ω.

The gas concentration sensor may be employed to sense an exhaust gas of an automotive engine.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings:

FIG. 4 is a flowchart of a subprogram used to determine the impedance of a sensor element;

FIG. 5 is a flowchart of a subprogram used to determine a duty cycle of a heater power supply control signal;

DESCRIPTION OF THE PREFERRED EMBODIMENTS

Figure 1:
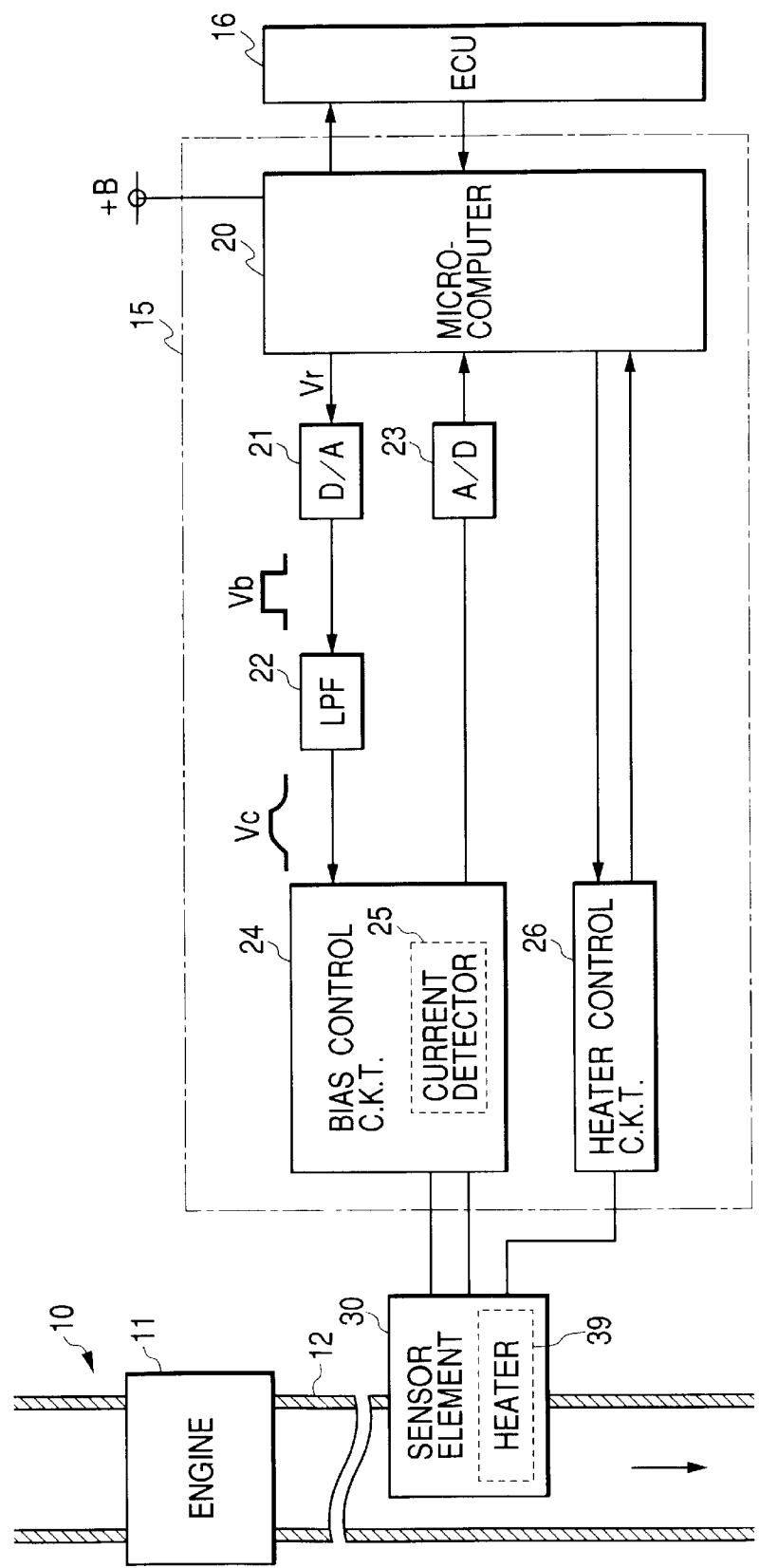
FIG. 1 is a block diagram which shows an air-fuel ratio control system equipped with a heater control system according to the first embodiment of the invention.

Referring now to the drawings, wherein like numbers refer to like parts in several views, particularly to FIG. 1, there is shown a gas sensor control system according to the first embodiment of the invention which is installed in an air-fuel ratio measuring device 15 used with an air-fuel ratio control system for automotive vehicles. The air-fuel ratio control system is designed to control the quantity of fuel injected into an internal combustion engine as a function of an output of the air-fuel ratio measuring device 15 under feedback (F/B) control to bring the air-fuel ratio into agreement with a target value. The air-fuel ratio measuring device 15 measures the concentration of oxygen ($O_2$) contained in exhaust gasses of the engine using an output of a limiting current oxygen sensor 30 (will be referred to as an A/F sensor below) and determines an air-fuel ratio. The air-fuel ratio measuring device 15 also has installed therein a heater control system which works to determine the impedance of a sensor element of the A/F sensor 30 and control the power supply to a heater built in the A/F sensor 30 for ensuring desired activation of the A/F sensor 30.

In FIG. 1, the air-fuel ratio measuring device 15 includes a microcomputer 20. The microcomputer 20 communicates with an electronic control unit (ECU) 16 which works as an engine control unit and performs a fuel injection control operation and an ignition control operation. The A/F sensor 30 is installed in an exhaust pipe 13 extending from a body 11 of the engine 10 and responsive to application of voltage from the microcomputer 20 to output an limiting current signal whose level changes linearly in proportion to the concentration of oxygen contained in the exhaust gasses.

The microcomputer 20 consists essentially of a CPU, a ROM, a RAM, etc. and executes a given control program to control a bias control circuit 24 and a heater control circuit 26 as will be described later in detail. The microcomputer 20 connects with a terminal +B of a storage battery installed in the vehicle and operates with a power supply therefrom.

The A/F sensor 30 is implemented by a so-called laminated sensor made of a lamination of a sensor element and a heater.

Figure 2:
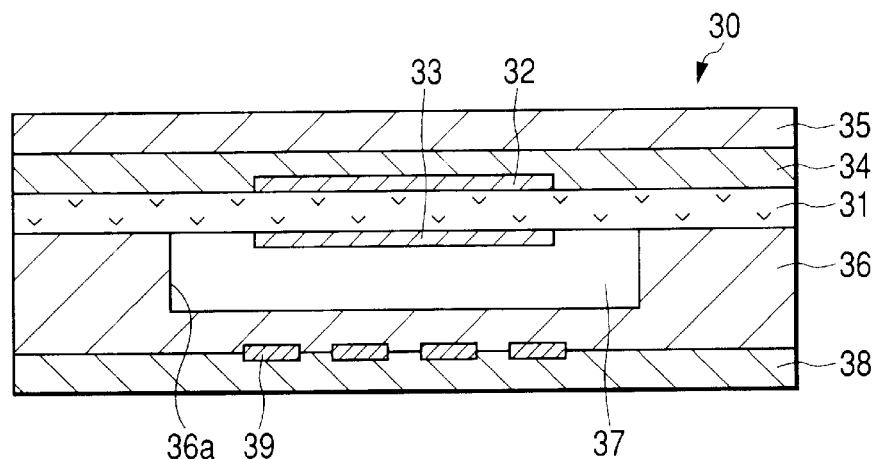
FIG. 2 is a longitudinal sectional view which shows an air-fuel ratio sensor in which a heater is controlled by the heater control system of FIG. 1.

An internal structure of the A/F sensor 30 will be described with reference to FIG. 2. FIG. 2 is a longitudinal sectional view as taken along a line extending in a lengthwise direction of the A/F sensor 30. The A/F sensor 30 is made of a lamination of a solid electrolyte layer 31, a porous diffusion resistance layer 34, a gas shield layer 35, a spacer 36, and a heater substrate 38. The solid electrolyte layer 31 is formed by an oxygen ion conductive layer made of a partially stabilized zirconia and has installed on opposed surfaces thereof a target gas electrode 32 and a reference gas electrode 33. The target gas electrode 32 is exposed to a target gas or exhaust gases of the engine 10. The reference gas electrode 33 is exposed to the air within a reference gas chamber 37. The air is used as a reference gas in determination of concentration of oxygen contained in the exhaust gasses. The porous diffusion resistance layer 34 is made of an alumina ceramic having a porosity of approximately 10%. The gas shield layer 35 is made of a dense alumina ceramic impermeable to gasses. The spacer 36 is made of a dense alumina ceramic which has an electric isolation property and is impermeable to gasses. The spacer 36 has formed therein a groove 36a working as the reference gas chamber 37. The heater substrate 38 is attached to the spacer 36 which has a heater 39 disposed in a surface thereof. The heater 39 is made of a resistance element which generates heat with a power supply.

Referring back to FIG. 1, the air-fuel ratio measuring device 15 also includes a D/A converter 21, a low-pass filter 22, and an A/D converter 23. The microcomputer 20 provides a bias command signal Vr to the D/A converter 21 for applying the voltage to the A/F sensor 30. The D/A converter 21 converts the input into an analog signal V1 and outputs it to the low-pass filter 22. The low-pass filter 22 removes high-frequency components from the analog signal V1 to produce a voltage signal V2 which is, in turn, inputted to the bias control circuit 24. The bias control circuit 24 is responsive to the voltage signal V2 to selectively apply an air-fuel ratio measuring voltage and a sensor element impedance measuring voltage, as will be described later in detail, to the A/F sensor 30. Specifically, when it is required to measure the air-fuel ratio using the A/F sensor 30, the voltage selected as a function of the measured air-fuel ratio is applied to the A/F sensor 30. Alternatively, when it is required to measure the impedance of a sensor element (i.e., the solid electrolyte layer 31) of the A/F sensor 30, the sensor element impedance measuring voltage having a given frequency and a given time constant is applied to the A/F sensor 30 in the form of a single shot. The impedance of the sensor element will also be refereed to as a sensor element impedance below.

The bias control circuit 24 includes a current measuring circuit 25. The A/F sensor 30, when applied with the voltage, produces a limiting current as a function of an oxygen content in exhaust gasses. The current measuring circuit 25 measures the limiting current outputted from the A/F sensor 30. An output of the current measuring circuit 25 is inputted to the microcomputer 20 through the A/D converter 23.

The heater control circuit 26 works as a heater driver which is responsive to a heater control signal provided in the form of a pulse signal by the microcomputer 20 to control a power supply to the heater 39. Specifically, the microcomputer 20 controls the duty cycle of the heater control signal as a function of the sensor element impedance of the A/F sensor 30. The heater control circuit 26 is responsive to the heater control signal to change an on-time for which the heater 39 is turned on or energized to regulate the quantity of power supplied to the heater 39.

The operation of the air-fuel ratio measuring device 15 will be described below.

Figure 3:
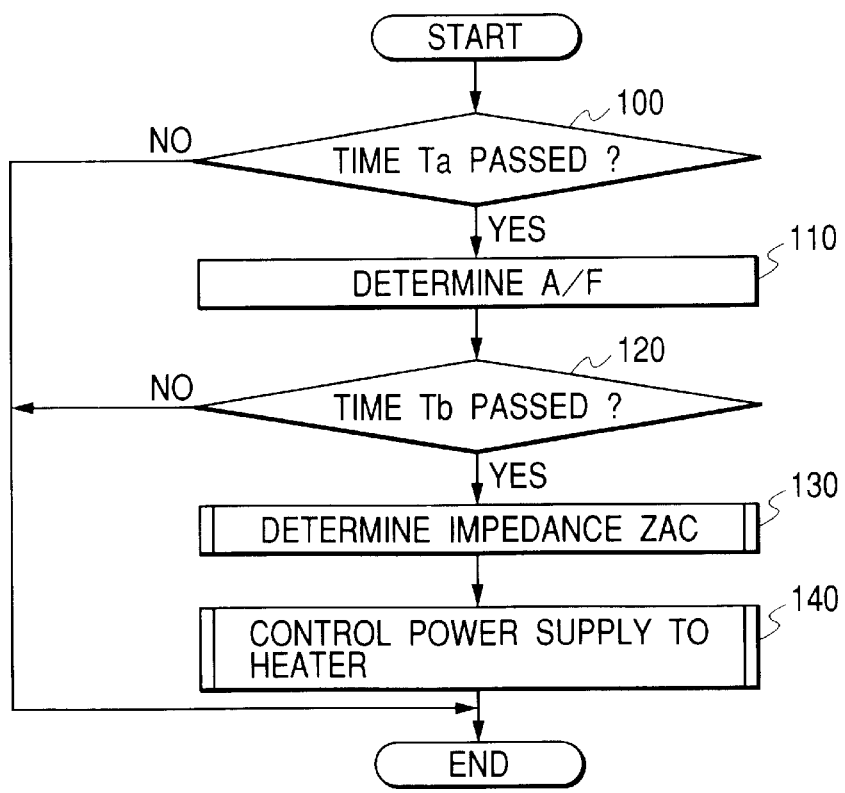
FIG. 3 is a flowchart of a main program performed to control a power supply to a heater.

FIG. 3 is a flowchart of a maim program performed by the microcomputer 20 upon turning on thereof.

After entering the program, the routine proceeds to step 100 wherein it is determined whether a preselected period of time Ta has passed since previous measurement of the air-fuel ratio or not. The preselected period of time Ta corresponds to a measurement cycle of the air-fuel ratio and is, for example, 4 msec. If a NO answer is obtained in step 100, then the routine repeats step 100. Alternatively, if a YES answer is obtained, then the routine proceeds to step 110 for measuring the air-fuel ratio.

In step 110, the microcomputer 20 applies the voltage across the electrodes 32 and 33 of the A/F sensor 30 to measure a sensor current (i.e., a limiting current) flowing therethrough using the current measuring circuit 25, determines an input voltage as a function of the sensor current, and applies it across the electrodes 33 and 34 of the A/F sensor 30. The microcomputer 20 converts the sensor current into a corresponding air-fuel ratio by look-up using a given current-A/F ratio map and outputs it to the ECU 16.

The routine proceeds to step 120 wherein it is determined whether a preselected period of time Tb has passed or not since the sensor element impedance ZAC, as will be discussed later in detail, was measured previously. The preselected period of time Tb corresponds to a measurement cycle of the sensor element impedance ZAC and is determined depending upon, for example, operating conditions of the engine 10. For example, when the engine 10 is in a normal operating condition in which a change in air-fuel ratio is relatively small, Tb=2 sec. When the engine 10 is in a start-up and transient conditions in which the air-fuel ratio changes greatly, Tb=128 msec.

If a YES answer is obtained in step 120, then the routine proceeds to step 130 wherein the sensor element impedance ZAC is determined using a so-called sweep method. The routine proceeds to step 140 wherein a power supply to the heater 39 is controlled. Alternatively, if a NO answer is obtained in step 120, then the routine returns back to step 100. The operations in step 130 and 140 will be discussed in detail below with reference to FIGS. 4 and 5, respectively.

After entering step 130, the routine proceeds to step 131 shown in FIG. 4 wherein the output of the bias command signal Vr is controlled to change a voltage Vp now provided to the A/F sensor 30 to the positive side instantaneously, thereby applying the sensor element impedance measuring voltage to the A/F sensor 30. The applied duration of the sensor element impedance measuring voltage is several tens to one hundred μsec. in light of frequency characteristics of the A/F sensor 30.

The routine proceeds to step 132 wherein a change a ΔV in voltage Vp and a change ΔI in sensor current measured by the current measuring circuit 25 are determined. The routine proceeds to step 133 wherein the sensor element impedance ZAC is calculated using the voltage change ΔV and the current change ΔI according to the relation of ZAC=ΔV/ΔI. The routine returns back to the program of FIG. 3.

The measurement of the sensor element impedance ZAC is, as discussed above, achieved by elevating the voltage Vp being applied to the A/F sensor 30 instantaneously to produce the sensor element impedance measuring voltage having a given time constant. After the elapse of a given time following application of the sensor element impedance measuring voltage to the A/F sensor 30, the peak of a current output from the A/F sensor 30 appears. This rise in the current output is measured as the current change ΔI and used to determine the sensor element impedance ZAC along with the voltage change ΔV. The application of the sensor element impedance measuring voltage to the A/F sensor 30 is accomplished through the low-pass filter 22 and the bias control circuit 24, thereby avoiding an excessive rise in the current output from the A/F sensor 30, which results in improved measurement accuracy of the sensor element impedance ZAC.

The determination of the sensor element impedance ZAC may alternatively be accomplished by producing a change in current flowing through the A/F sensor 30 and measuring a resulting change in voltage applied across the A/F sensor 30.

Figure 7:
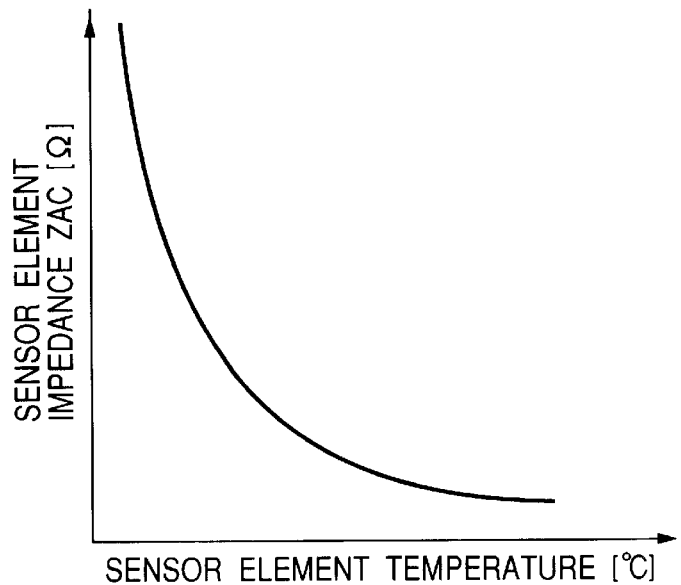
FIG. 7 is a graph which shows a relation between a sensor element impedance and a sensor temperature.

The sensor element impedance ZAC bears a relation, as shown in a graph of FIG. 7, to the temperature of the sensor element. The graph shows that the sensor element impedance ZAC increases greatly as the temperature of the sensor element decreases.

The control of power supply to the heater 39 performed in step 140 in FIG. 3 will be described below with reference to FIG. 5. The microcomputer 20 works to regulate the power supply to the heater 39 through the heater control circuit 26 under feedback control as a function of a difference between a value of the sensor element impedance ZAC and a target one. Specifically, the microcomputer 20 performs the so-called PI (Proportional plus Integral) control using a proportional term (P) and an integral term (I) of an IP control function as calculated cyclically. Proportional and integral gains are changed as a function of the value of the sensor element impedance ZAC. Of course, the microcomputer 20 may alternatively employ the so-called PID control function.

The determination of the integral and proportional gains in the microcomputer 20 will be described with reference to FIGS. 8(a) and 8(b).

A controlled range of the sensor element impedance ZAC is defined across an impedance target value ZACtg. For instance, if the impedance target value ZACtg is 28Ω, the impedance controlled range is defined between 26Ω to 30Ω (i.e., ZACtg±2Ω). When the sensor element impedance ZAC is lower than the impedance controlled range, that is, on a side where the temperature of the sensor element is higher than that within the impedance controlled range, the integral and proportional gains are set to greater values for avoiding excessive rising of the temperature of the sensor element. TH1, as indicated in the drawings, is a lower limit of the impedance controlled range (i.e., TH1=26Ω) which is used as a threshold value in switching the gains. The PI control may be performed in this embodiment by modifying at least one of the proportional gain and the integral gain as a function of the sensor element impedance ZAC.

Figure 8A:
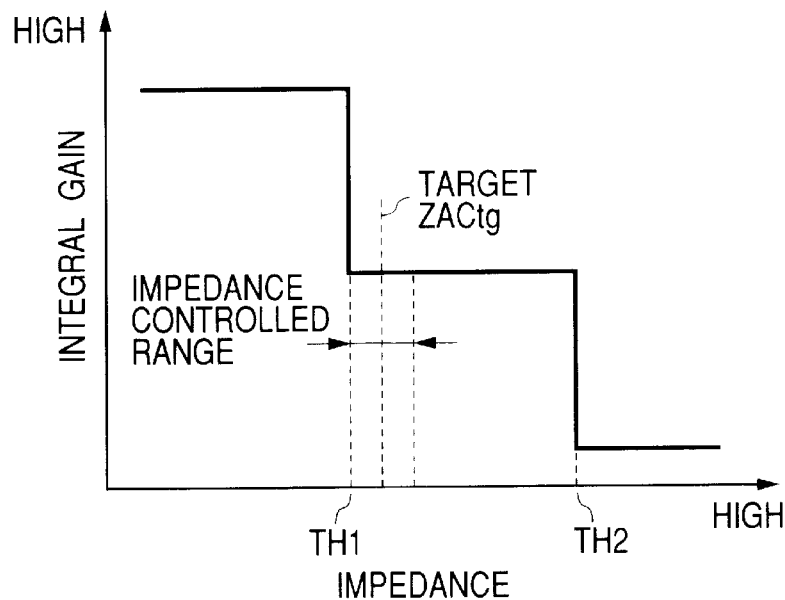
FIG. 8(a) is an illustration which shows a relation between an integral gain and a sensor element impedance.

TH2, as indicated in FIG. 8(a), is a threshold value through which the sensor element impedance ZAC passes when it is dropping during activation of the sensor element of the A/F sensor 30. When the sensor element impedance ZAC is higher than the threshold value TH2, the integral gain is limited to zero or a minimum possible value. The threshold value TH1 is 48Ω in this embodiment.

Figure 8B:
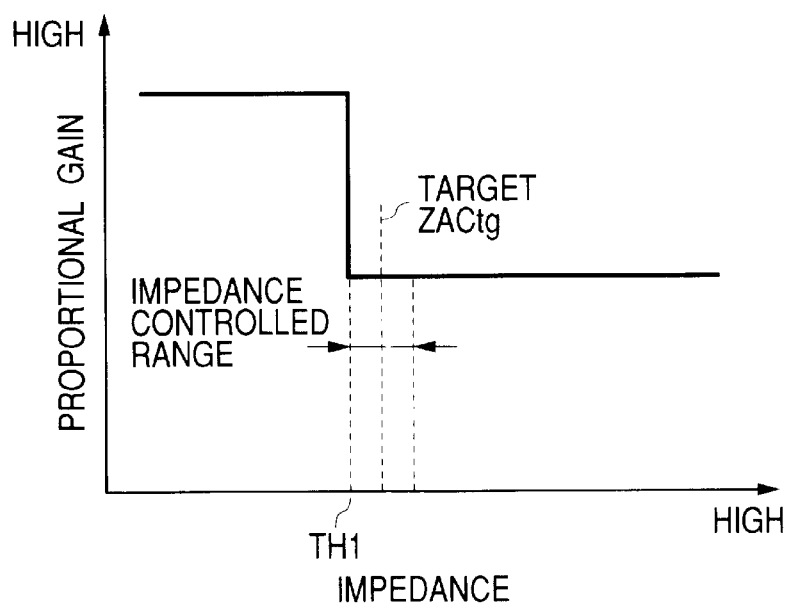
FIG. 8(b) is an illustration which shows a relation between a proportional gain and a sensor element impedance.

The microcomputer 20 of this embodiment is designed to change the proportional and integral gains of PI control parameters using the gain-impedance maps, as illustrated in FIGS. 8(a) and 8(b), to control the power supply to the heater 39 under feedback control. Specifically, the microcomputer 20 controls the power supply to the heater 39 through the heater control circuit 26 in three control modes I, II, and III, as discussed below, upon variation in sensor element impedance ZAC, for example, after the A/F sensor 30 is turned on. In mathematical equations, as referred to below, Kp1 and Kp2 are constants of proportion, i.e., proportional gains. Kp2 is approximately twice Kp1. Ki is an integration constant, i.e., integral gain.

First Control Mode I

When the sensor element impedance ZAC is higher than the threshold value TH2 (i.e., 48Ω), that is, when the temperature of the sensor element is low, the microcomputer 20 determines the duty cycle Duty of the heater control signal (i.e., the amount of power supply to the heater 39) only using the proportional term according to an equation below.

$$\text{Duty} = Kp1 \times (ZACtg - ZAC) \tag{1}$$

Second Control Mode II

When the sensor element impedance ZAC falls within a range of TH1 to TTH2 (i.e., 26Ω to 48Ω), the microcomputer 20 determines the duty cycle Duty of the heater control signal using both the proportional constant Kp1 and the integral constant Ki according to an equation below.

$$\text{Duty} = Kp1 \times (ZACtg - ZAC) + \Sigma\{Ki \times (ZACtg - ZAC)\} \tag{2}$$

Third Control Mode III

When the sensor element impedance ZAC is less than or equal to the threshold value TH1 (i.e., 26Ω), the microcomputer 20 determines the duty cycle Duty of the heater control signal using the proportional constant Kp2 and the integral constant Ki according to an equation below.

$$\text{Duty} = Kp2 \times (ZACtg - ZAC) + \Sigma\{Ki \times (ZACtg - ZAC)\} \qquad (3)$$

The control of power supply to the heater 39 performed in step 140 of FIG. 3 will be described below in detail with reference to a subroutine of FIG. 5.

First, in step 141, it is determined whether a condition in which the control of power supply to the heater 39 should be initiated is met or not. For example, it is determined whether the sensor element impedance ZAC is greater than or equal to a given threshold value TTH3 of 65Ω or not. Alternatively, it is determined whether the elapsed time from start-up of the engine 10 still lies within a given time range or not. Usually, immediately after start-up of the engine 10, the temperature of the A/F sensor 30 is low. In this case, the sensor element impedance ZAC is higher than the threshold value TH3. A YES answer is, thus, obtained in step 141 meaning that the control of power supply to the heater 39 should be initiated, and the routine proceeds to step 142 wherein a duty cycle-controlled signal (i.e., the heater control signal), which will also be referred to as a heater power supply control signal below), provided to turn on and off the heater control circuit 26 is kept in duty cycle at 100% to supply the power to the heater 39 fully.

Alternatively, if the temperature of the sensor element has already risen, a NO answer is obtained in step 141. The routine, thus, proceeds to step 143 wherein it is determined whether the sensor element impedance ZAC is smaller than the threshold value TH2 (i.e., 48Ω) or not. If a YES answer is obtained, then the routine proceeds to step 144 wherein it is determined whether the sensor element impedance ZAC is smaller than the threshold value TH1 (i.e., 26Ω) or not. If a YES answer is obtained, then the routine proceeds to step 147.

If a NO answer is obtained in step 143 meaning that ZAC≧TH2, then the routine proceeds to step 145 wherein the duty cycle Duty of the power supply control signal (i.e., the heater control signal) is determined using Eq. (1), as described above. The routine proceeds to step 149 wherein a guard operation, as shown in FIG. 6(b), is performed on the duty cycle Duty, as determined in step 145 and then returns back to the routine of FIG. 3.

Figure 6A:
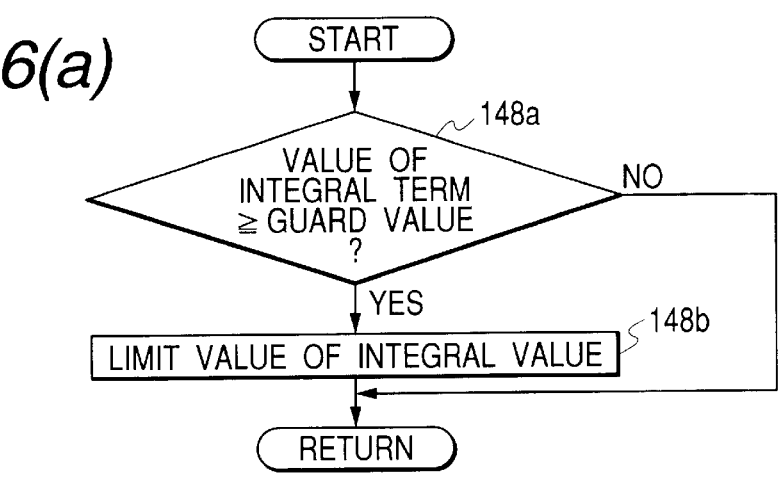
FIG. 6(a) is a flowchart of a subprogram used to limit an integral gain in a PI control equation.
Figure 6B:
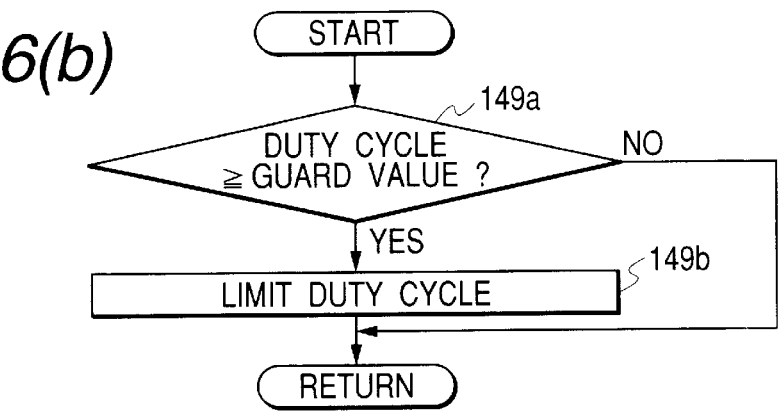
FIG. 6(b) is a flowchart of a subprogram used to limit a duty cycle of a heater power supply control signal.

In step 149a of FIG. 6(b), it is determined whether the duty cycle Duty is higher than or equal to a given upper limit (i.e., a guard value) or not. If a YES answer is obtained, then the routine proceeds to step 149b wherein the duty cycle Duty is guarded with the upper limit. Specifically, a maximum value of the duty cycle DUTY is restricted to the upper limit.

If a NO answer is obtained in step 144 meaning that TH1≦ZAC<TH2, then the routine proceeds to step 146 wherein the duty cycle Duty of the power supply control signal is determined using Eq. (2), as described above.

If a YES answer is obtained in step 144 meaning that ZAC<TH1, then the routine proceeds to step 147 wherein the duty cycle Duty of the power supply control signal is determined using Eq. (3), as described above.

After step 146 or 147, the routine proceeds to step 148 wherein the value of the integral term ΣKi (ZACtg−ZAC), as determined in step 146 or 147, is guarded in a subroutine as illustrated in FIG. 6(a). In step 148a, it is determined whether the value of the integral term of the IP control equation is higher than or equal to a given upper limit (i.e., a guard value) or not. If a YES answer is obtained, then the routine proceeds to step 148b wherein the value of the integral term is guarded with the upper limit. Specifically, a maximum value of the integral term is restricted to the upper limit. After such restriction of the integral term, the duty cycle Duty of the power supply control signal is re-calculated. The operation in step 148 may alternatively be performed within each of steps 146 and 147 to determine the duty cycle Duty of the power supply control signal using the restricted value of the integral term or for a following program cycle without re-calculating the duty cycle Duty using the restricted value of the integral term in this program cycle.

After step 148, the routine proceeds to step 149 wherein the above described guard operation is performed on the duty cycle Duty.

The guard values (i.e., the upper limits) used in step 148 and 149 may be determined as a function of the temperature of the sensor element, respectively. For example, when the sensor element impedance ZAC is shifted out of the controlled range to the lower-impedance side, that is, when the temperature of the sensor element is increased, and a YES answer is obtained in step 144, the guard value may be decreased.

If the sensor element impedance ZAC rises above the threshold value TH2 (i.e., 48Ω) due to a drop in temperature of exhaust gas of the engine 10 after the A/F sensor 30 is activated once, the A/F sensor 30 may become inactivated. In this case, when the sensor element impedance ZAC drops below the threshold value TTH2 again, the value of the integral term of the PI control equation, as cumulated so far, is preferably reset to zero in supplying the power to the heater 39 to reactivate the A/F sensor 30. In practice, when a condition of ZAC<TH2 is encountered, that is, a YES answer is obtained in step 143 for the first time, the value of the integral term is reset to zero or a value preselected near zero.

Figure 9:
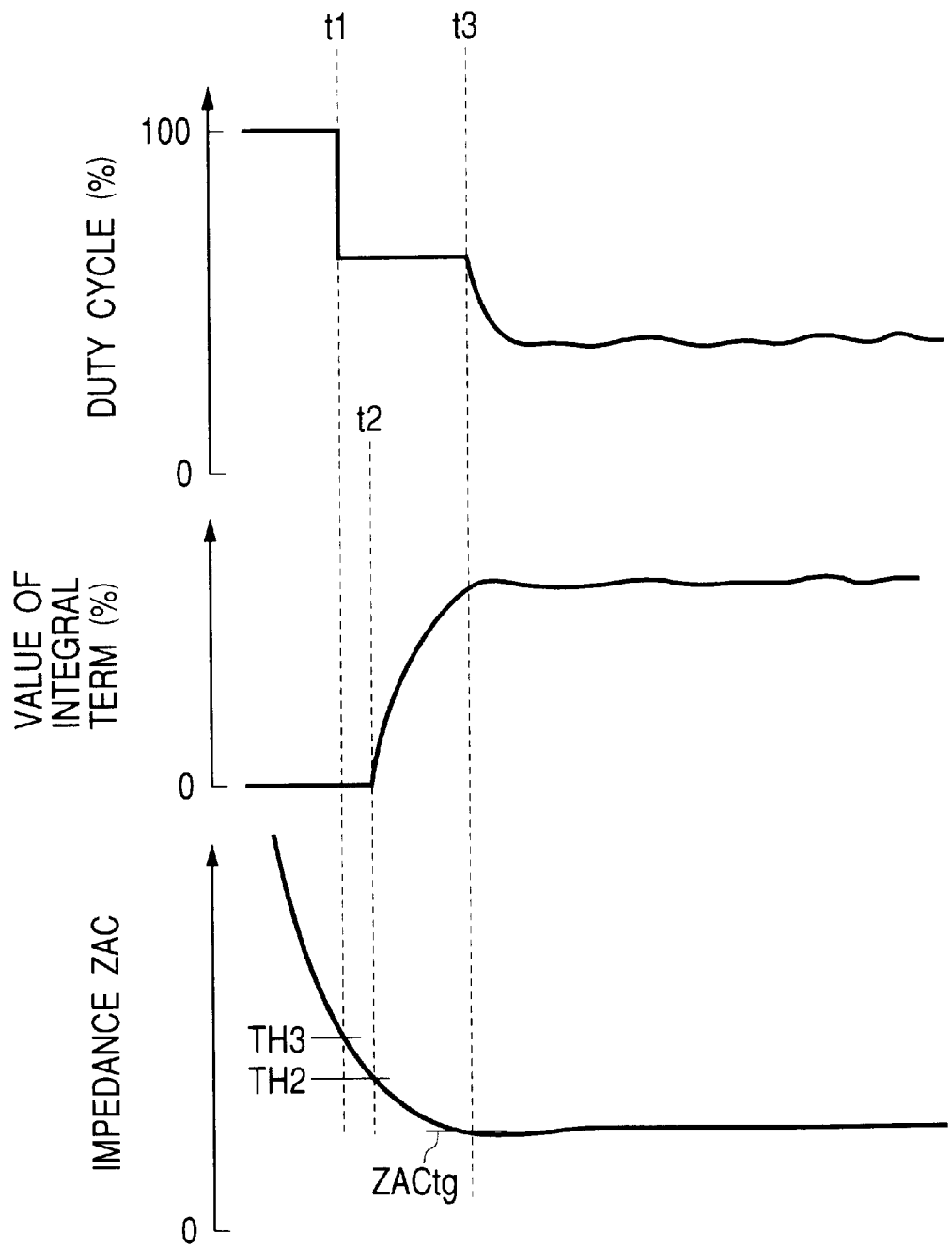
FIG. 9 is a time chart which shows changes in duty cycle of a heater power supply control signal, an integral gain, and a sensor element impedance.

FIG. 9 illustrates a relation among the duty cycle Duty of the heater power supply control signal, the value of the integral term of the IP control equation, and the sensor element impedance ZAC when the engine 10 is in the startup mode, that is, when the A/F sensor 30 is being activated.

Immediately after the engine startup, the duty cycle Duty of the heater power supply control signal is set to 100% to supply the power to the heater 39 fully. After time t1 when a condition ZAC≦TH3 (i.e., 65Ω) is encountered, the power supply to the heater 39 is controlled in the feedback mode. Specifically, after time t1, the duty cycle Duty of the heater power supply control signal is determined only using the proportional term while keeping the value of the integral term at zero (0). At time t2 when a condition of ZAC<TH2 is encountered, the value of the integral term starts to be calculated. Specifically, after time t2, the PI control is initiated using both the proportional and integral terms in the IP control equation. Between times t1 and t3, the duty cycle Duty is guarded in the manner as described above. At time t3 when the sensor element impedance ZAC drops below the target value ZACtg, a difference between the sensor element impedance ZAC and the target value ZACtg is reversed in orientation or sign. After time t3, the duty cycle Duty of the heater power supply control signal is decreased away from the guard value.

In the course of activation of the A/F sensor 30, the value of the integral term increases undesirably, thus resulting in overshoot of the sensor element impedance ZAC. This problem is, however, eliminated in this embodiment by limiting the value of the integral term to the guard value.

If the engine 10 undergoes a fuel cut after completion of activation of the A/F sensor 30, it will cause the temperature of the sensor element to drop instantaneously due to a drop in temperature of exhaust gas. In this case, the duty cycle Duty of the heater power supply control signal is determined in this embodiment using the values of the integral and proportional terms as derived so far. This ensures the stability of control of the heater 39 even if such an instantaneous change in temperature arises.

As apparent from the above discussion, the gas sensor control system of this embodiment works to eliminate an excessive rise in temperature of the sensor element when activating the sensor element, thereby protecting the sensor element against thermal breakage.

Further, when the sensor element impedance ZAC is shifted out of the controlled range due to, for example, a rise in temperature of exhaust gas of the engine 10 after the A/F sensor 30 is activated once, the microcomputer 20 increases the proportional gain to accelerate convergence of the sensor element impedance ZAC on the target value ZACtg. This avoids thermal overheating of the sensor element of the A/F sensor 30 after activation thereof.

Figure 10:
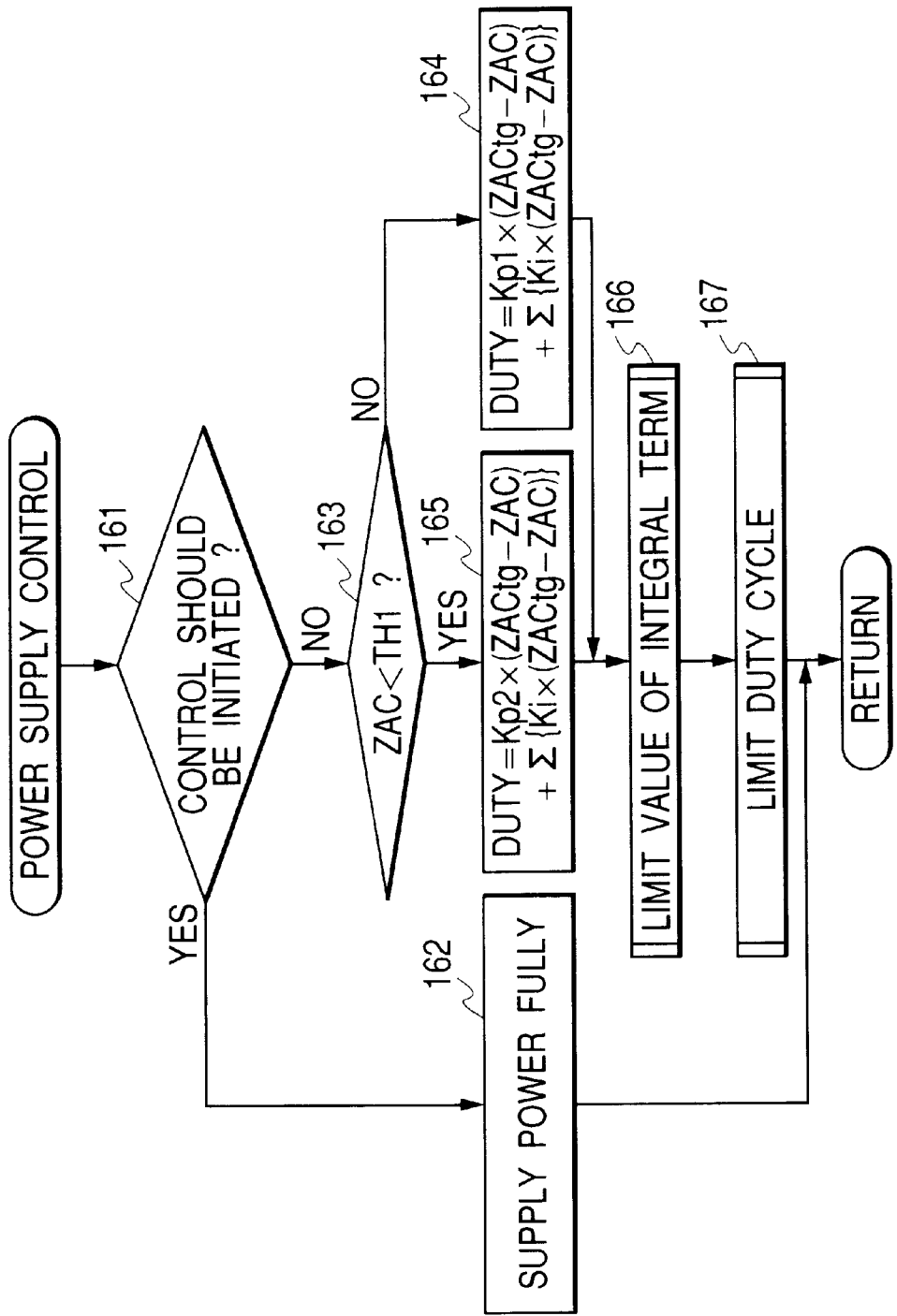
FIG. 10 is a flowchart of a subprogram used to determine a duty cycle of a heater power supply control signal according to the second embodiment of the invention.

FIG. 10 shows the heater power supply control performed in step 140 of FIG. 3 according to the second embodiment of the invention.

First, in step 161, it is determined whether a condition in which the control of power supply to the heater 39 should be initiated is met or not in the same manner as in FIG. 5. If a YES answer is obtained, the routine proceeds to step 162 wherein the heater power supply control signal whose duty cycle is approximately 100% is provided to supply the power to the heater 39 fully.

If a NO answer is obtained in step 161. The routine proceeds to step 163 wherein it is determined whether the sensor element impedance ZAC is smaller than the threshold value TH1 (i.e., 26Ω) or not. If a NO answer is obtained (ZAC>TH1), then the routine proceeds to step 164 wherein the duty cycle Duty of the power supply control signal is determined using Eq. (2), as described above. Alternatively, if a YES answer is obtained (ZAC<TH1), then the routine proceeds to step 165 wherein the duty cycle Duty of the power supply control signal is determined using Eq. (3), as described above.

After step 164 or 165, the routine proceeds to step 166 wherein the value of the integral term ΣKi (ZACtg−ZAC) is guarded in the same manner as in step 148 of FIG. 5.

The routine proceeds to step 167 wherein the value of the duty cycle Duty is guarded in the same manner as in step 149 of FIG. 5.

Figure 11:
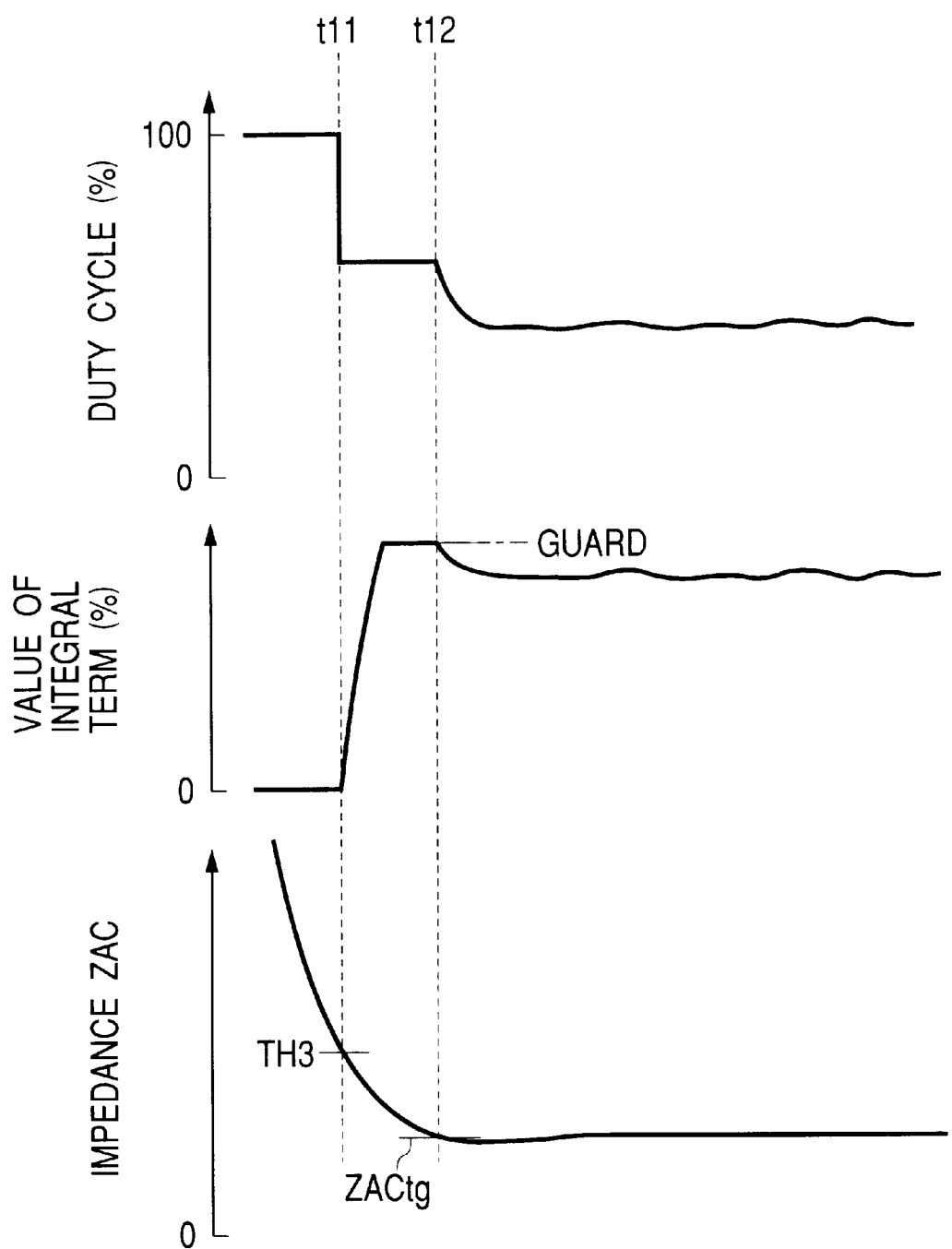
FIG. 11 is a time chart which shows changes in duty cycle of a heater power supply control signal, an integral gain, and a sensor element impedance in the second embodiment.

FIG. 11 illustrates a relation among the duty cycle Duty of the heater power supply control signal, the value of the integral term of the PI control equation, and the sensor element impedance ZAC when the engine 10 is in the startup mode in the second embodiment.

Immediately after the engine startup, the duty cycle Duty of the heater power supply control signal is set to 100% to supply the power to the heater 39 fully. After time t11 when a condition ZAC≦TH3 (i.e., 65Ω) is encountered, the power supply to the heater 39 is controlled in the feedback mode. Specifically, after time t1, the value of the integral term starts to be calculated. The duty cycle Duty of the heater power supply control signal is determined using the proportional and integral terms in the PI control equation. A maximum value of the integral term is limited to the guard value in order to avoid the overshooting of the sensor element impedance ZAC. At time t12, the sensor element impedance ZAC drops below the target value ZACtg, so that a difference therebetween is reversed in orientation or sign. After time t12, the values of the integral term and the duty cycle Duty of the heater power supply control signal are decreased away from the guard values, respectively.

The gas sensor control system according to the third embodiment will be described below which is designed to determine the target value of the sensor element impedance ZAC in two steps during transition of the A/F sensor 30 from an inactivated to activated status. Specifically, the sensor element impedance ZAC is brought into agreement with two target values: initial target value TG2 and final target value TG1 in a stepwise fashion. The final target value TG1 is 28Ω. The initial target value TG2 is set higher than TG1. For instance, the initial target value TG2 is TG1 plus 5Ω (=33Ω). Other arrangements and operations of the gas sensor control system of this embodiment are identical with those in the first embodiment, and explanation thereof in detail will be omitted here.

Figure 12:
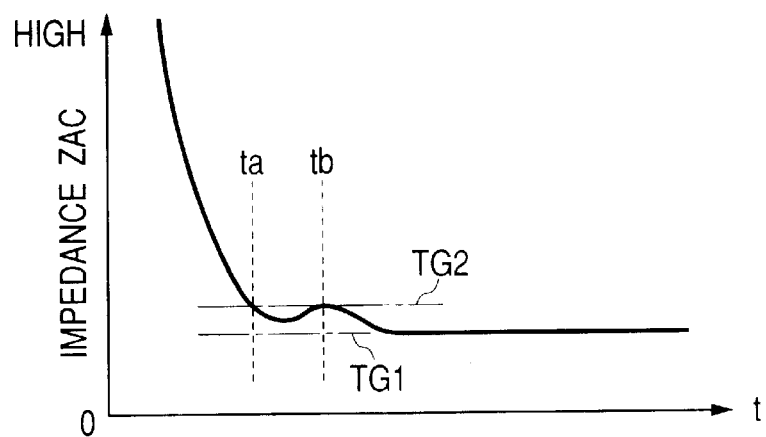
FIG. 12 is a time chart which shows a variation in sensor element impedance at startup of an engine.

FIG. 12 illustrates a change in the sensor element impedance ZAC when the engine 10 is in the startup mode in the third embodiment.

At an initial stage of heating the sensor element of the A/F sensor 30, the heater control circuit 26 increases the temperature of the sensor element through the heater 39 so that the sensor element impedance ZAC may be brought into agreement with the initial target value TG2. Upon reading the initial target value TG2 at time ta, the sensor element impedance ZAC overshoots instantaneously and returns back to it again at time tb. At time tb, the target value of the sensor element impedance ZAC is switched from TG2 to TG1. This causes the sensor element impedance ZAC to be converged on the final target value TG1 after time tb.

The switching of the initial target value TG2 to the final target value TG1 may alternatively be made after the elapse of a predetermined period of time (e.g., a few seconds) from when the sensor element impedance ZAC reaches the initial target value TG2.

The two-step control of the sensor element impedance ZAC in this embodiment serves to converge the sensor element impedance ZAC at the final target value TG1 without overshooting, thereby avoiding an excessive rise in temperature of the sensor element when the A/F sensor 30 is activated.

The initial target value TG2 is preferably defined within a range of the final target value TG1 plus 10Ω. The difference between the initial target value TG2 and the final target value TG1 may be determined in light of an overshoot of the sensor element impedance ZAC.

Two or more initial target values may be provided. For instance, in a case where the final target value TG1 is 28Ω, the target value of the sensor element impedance ZAC may be switched from 34Ω to 31Ω and to 28Ω.

The invention may be embodied in modifications as discussed below.

In the first embodiment, the duty cycle Duty of the heater power supply control signal is determined without use of the integral term of the PI control equation until the sensor element impedance ZAC reaches the threshold value TH2. In other words, the integral gain is set to zero (0) until the sensor element impedance ZAC reaches the threshold value TH2. The integral gain, however, may be set to a smaller value preselected near zero (0).

In the first embodiment, the P control is performed only using the proportional term of the PI control equation until it is decided that the sensor element impedance ZAC reaches the threshold value TH2, after which the PI control on which both the proportional and integral terms reflect is initiated, but however, the PI control may be initiated after the elapse of a predetermined time period from the start of the P control. The time the PI control should be initiated may be determined based on results of tests.

In the above embodiments, the proportional gain is increased (in steps 146 and 147 of FIG. 5) when the sensor element impedance ZAC is lower than the controlled range thereof, that is, when the temperature of the sensor element is higher than a range corresponding to the controlled range, however, only the integral gain or both the proportional and integral gains may alternatively be increased.

The A/F sensor 30 has a temperature characteristic, as shown in FIG. 7, in which a change in temperature of the sensor element results in a change in sensor element impedance ZAC. Therefore, within the F/B controlled range of the sensor element impedance ZAC, either or both of the proportional and integral gains of the PI control equation may be increased as the sensor element impedance ZAC decreases.

The mathematical determination of the duty cycle Duty of the heater power supply control signal may be made by using a basic term which is defined in the PI control equation and includes a parameter of the sensor element impedance ZAC. For instance, the value of the basic term is determined by look-up using a map or mathematical calculation so that it increases with a decrease in sensor element impedance ZAC. The values of the proportional and integral terms are added to the value of the basic term to determine the duty cycle Duty of the heater power supply control signal (i.e., Duty=basic term+proportional term+integral term). In this case, the duty cycle Duty may be determined only using the value of the basic term until the sensor element impedance ZAC reaches a preselected value of the impedance of the sensor element during thermal activation, after which it may be determined by adding the value of the integral term to that of the basic term.

Figure 13:
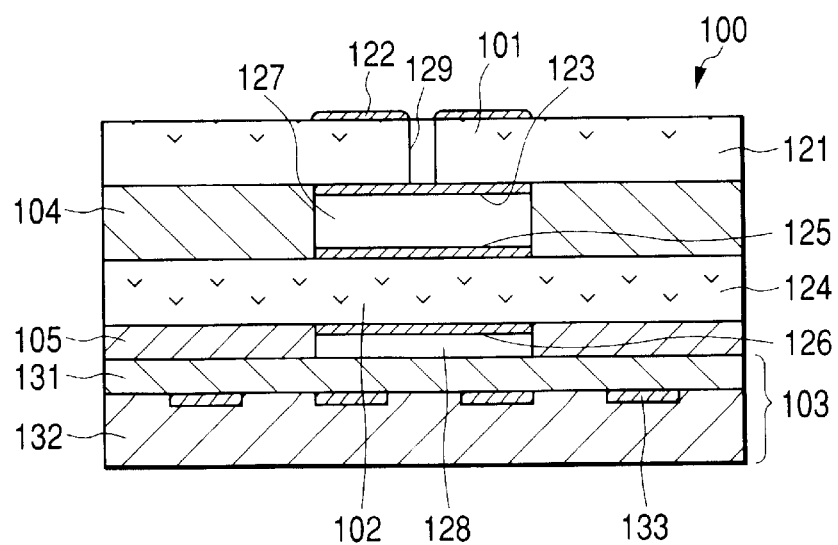
FIG. 13 is a cross sectional view which shows a first modification of an air-fuel ratio sensor which may be used in an air-fuel ratio control system.
Figure 14A:
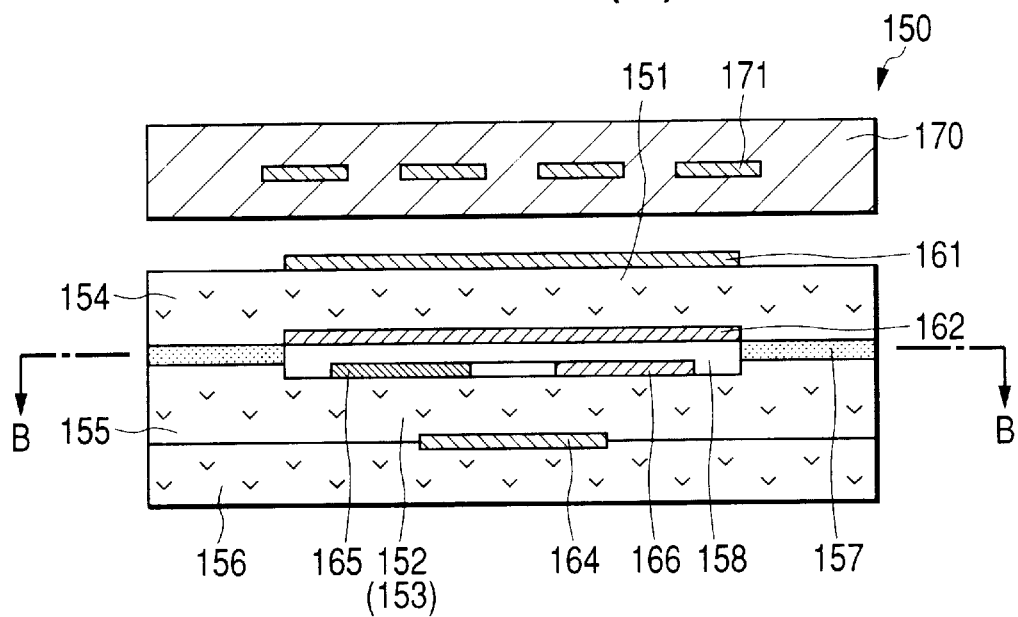
FIG. 14(a) is a cross sectional view which shows a second modification of an air-fuel ratio sensor which may be used in an air-fuel ratio control system.
Figure 14B:
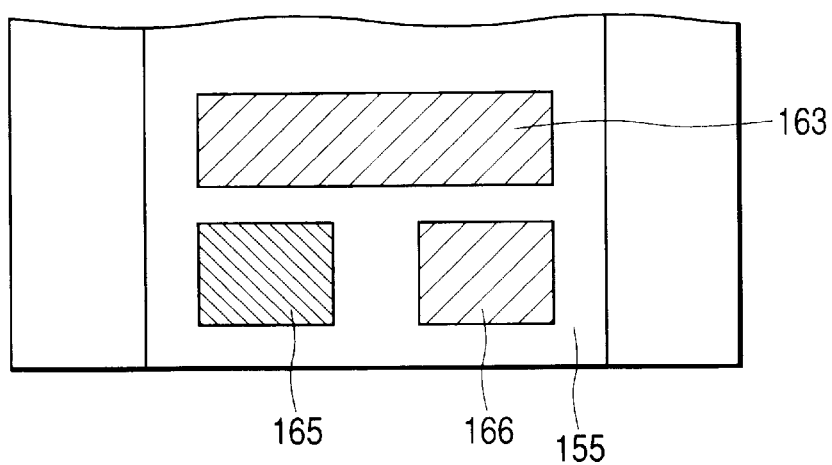
FIG. 14(b) is an illustration taken along the line B—B in FIG. 14(a).

The A/F sensor 30 may be replaced with one as illustrated either in FIG. 13 or FIGS. 14(a) and 14(b) which may have a single or multi-sensor cell structure designed to measure the concentration of nitrogen oxide (NOx), hydro carbon (HC), and/or carbon monoxide (CO).

The A/F sensor 100, as illustrated in FIG. 13, includes an oxygen pump cell 101, an oxygen sensor cell 102, and a heater layer 103 which are laid to overlap each other through spacers 104 and 105. The oxygen pump cell 102 is made up of a solid electrolyte layer 121 and a pair of pump electrodes 122 and 123 attached to opposed surfaces of the solid electrolyte layer 121. The oxygen sensor cell 102 is made up of a solid electrolyte layer 124 and a pair of sensor electrodes 125 and 126 attached to opposed surfaces of the solid electrolyte layer 124.

The spacers 104 and 105 are each made of an insulating material such as ceramic and have formed therein a measurement gas chamber 127 into which exhaust gasses of the engine 10 are admitted and an air chamber 128 into which the air is admitted as a reference gas, respectively. The heater layer 103 is made up of upper and lower insulating sheets 131 and 132 and a heating element 133 printed between the sheets 131 and 132.

The exhaust gasses of the engine 10 are introduced into the measurement gas chamber 127 through a diffusion path 129. The oxygen pump cell 101 works to produce an electric current as a function of the concentration of oxygen molecules ($O_2$) contained the exhaust gasses. The oxygen sensor cell 102 produces an electromotive force as a function of the concentration of oxygen contained in the exhaust gasses introduced into the measurement gas chamber 127. The voltage is applied across the pump electrodes 122 and 123 to bring the electromotive force produced by the oxygen sensor cell 102 into agreement with a constant value.

The A/F sensor 150, as illustrated in FIGS. 14(a) and 14(b), includes an oxygen pump cell 151, an oxygen sensor cell 152, and an oxygen concentration cell 153. The oxygen pump cell 151 is made of a solid electrolyte layer 154. The oxygen sensor cell 152 and the oxygen concentration cell 153 are made of a solid electrolyte layer 155. The solid electrolyte layers 154 and 155 are laid to overlap each other through a diffusion resistance layer 157. A solid electrolyte layer 156 is also attached to the solid electrolyte layer 155. The solid electrolyte layers 154 and 155 and the diffusion resistance layer 157 define a measurement gas chamber 158 into which the exhaust gasses of the engine 10 are introduced through the diffusion resistance layer 157.

The oxygen pump cell 151 has a pair of electrodes 161 and 162 formed on opposed surfaces of the solid electrolyte layer 154. The oxygen sensor cell 152 has a pair of electrodes 163 and 164 formed on opposed surfaces of the solid electrolyte layer 155. The oxygen concentration cell 153 has a pair of electrodes 165 and 166 which are formed on a surface of the solid electrolyte layer 155 exposed to the measurement gas chamber 158. Specifically, the electrodes 163, 165, and 166 are, as clearly shown in FIG. 14(b), arranged on the same surface of the solid electrolyte layer 155. One of the electrodes 165 and 166 of the oxygen concentration sensor 153 is implemented by an electrode designed to have a high catalytic activity, and the other is implemented by an catalytically-inactive electrode. A heater unit 170 is joined to an outer surface of the oxygen pump cell 151 which has a heater 171.

The oxygen pump cell 151 works to measure the concentration of oxygen contained in the exhaust gasses. The oxygen sensor cell 152 produces an electromotive force as a function of the concentration of oxygen within the measurement gas chamber 158. The voltage is applied across the electrodes 161 and 162 of the oxygen pump cell 151 so that the electromotive force produced by the oxygen sensor cell 152 may be kept constant. The quantity of oxygen consumed by the catalytic active electrode 165 is greater than the catalytic inactive electrode 166, so that the concentration of oxygen near the catalytically-inactive electrode 166 will be higher than that near the catalytically-active electrode 165. This causes an electromotive force which is positive on the side of the catalytically-inactive electrode 166 to be produced between the electrodes 165 and 166 of the oxygen concentration cell 153 as a function of the concentration of a specified flammable gas contained in the exhaust gasses.

The A/F sensors 30, 100, and 150 may also be designed to measure the concentration of a gas other than a specified component of exhaust gasses of the engine 10.

The operation of gas concentration sensors of types, as illustrated in FIGS. 13 to 14(b), are well known in the art, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A heater control apparatus comprising:
   a control circuit working to control a power supply to a heater used to heat a solid electrolyte-made sensor element of a gas concentration sensor up to a temperature at which the sensor element is activated to provide a desired gas concentration output;

a sensor element resistance determining circuit working to determine a resistance value of the sensor element of the gas concentration sensor; and a heater control variable determining circuit determining a heater control variable for controlling the power supply to the heater in said control circuit based on a value of an integral term in a control function which is determined as a function of a difference between the resistance value determined by said sensor element resistance determining circuit and a target value, said heater control variable determining circuit putting a limitation on increasing of the value of the integral term until the resistance value of the sensor element reaches a preselected value in the course of activation of the sensor element.

2. A heater control apparatus as set forth in claim 1, wherein said heater control variable determining circuit sets the value of the integral term to zero until the resistance value of the sensor element reaches the preselected value.

3. A heater control apparatus as set forth in claim 1, wherein said heater control variable determining circuit determines the heater control variable only using a value of a proportional term in the control function defined in proportional plus integral control until the resistance value of the sensor element reaches the preselected value in the course of activation of the sensor element, after which said heater control variable determining circuit determines the heater control variable using both the proportional term and the integral term.

4. A heater control apparatus as set forth in claim 1, wherein said heater control variable determining circuit sets the value of the integral term to a value defined near zero until the resistance value of the sensor element reaches the preselected value.

5. A heater control apparatus as set forth in claim 1, wherein said heater control variable determining circuit resets the value of the integral term when the resistance value of the sensor element reaches the preselected value during the activation of the sensor element.

6. A heater control apparatus as set forth in claim 1, said heater control variable determining circuit works to limit a maximum value of the integral term to a preselected guard value.

7. A heater control apparatus as set forth in claim 1, wherein said heater control variable determining circuit determines the heater control variable so as to supply power to the heater substantially fully at a given initial stage of increasing temperature of the heater and subsequently determines the heater control variable using the control function.

8. A heater control apparatus as set forth in claim 1, wherein said heater control variable determining circuit increases at least one of gains of the integral term and a proportional term in the control function defined in proportional plus integral control when the resistance value of the sensor element is shifted to a side on which temperature of the sensor element is increased out of a controlled range defined across the target value.

9. A heater control apparatus as set forth in claim 1, wherein said heater control variable determining circuit increases at least one of gains of the integral term and a proportional term in the control function defined in proportional plus integral control based on a temperature-resistance characteristic of the sensor element within a feedback controlled range in which the power supply to the heater is controlled as a function of the difference between the resistance value determined by said sensor element resistance determining circuit and the target value.

10. A heater control apparatus as set forth in claim 1, wherein the gas concentration sensor works to sense an exhaust gas of an automotive engine.

11. A heater control apparatus comprising:

a control circuit working to control a power supply to a heater used to heat a solid electrolyte-made sensor element of a gas concentration sensor up to a temperature at which the sensor element is activated to provide a desired gas concentration output;

a sensor element resistance determining circuit working to determine a resistance value of the sensor element of the gas concentration sensor; and a heater control variable determining circuit determining a heater control variable for controlling the power supply to the heater in said control circuit based on values of an integral and a proportional term of a control function used in proportional plug integral control which are each determined as a function of a difference between the resistance value determined by said sensor element resistance determining circuit and a target value, said heater control variable determining circuit increasing at least one of gains of the integral and proportional terms when the resistance value of the sensor element is shifted to a side on which temperature of the sensor element is increased out of a controlled range defined across the target value.

12. A heater control apparatus as set forth in claim 11, wherein said heater control variable determining circuit increases at least one of the gains of the integral and proportional terms based on a temperature-resistance characteristic of the sensor element within a feedback controlled range in which the power supply to the heater is controlled as a function of the difference between the resistance value determined by said sensor element resistance determining circuit and the target value.

13. A heater control apparatus as set forth in claim 11, wherein the gas concentration sensor works to sense an exhaust gas of an automotive engine.

14. A heater control apparatus comprising:

a control circuit working to control a power supply to a heater used to heat a solid electrolyte-made sensor element of a gas concentration sensor up to a temperature at which the sensor element is activated to provide a desired gas concentration output;

a sensor element resistance determining circuit working to determine a resistance value of the sensor element of the gas concentration sensor; and a heater control variable determining circuit determining a heater control variable for controlling the power supply to the heater in said control circuit as a function of a difference between the resistance value determined by said sensor element resistance determining circuit and a target value so as to bring the difference into agreement with the target value, said heater control variable determining circuit switching the target value between an initial value and a final value lower than the initial value during activation of the sensor element.

15. A heater control apparatus as set forth in claim 14, wherein said heater control variable determining circuit switches the target value from the initial value to the final value when the target value has first overshot the initial value and reached the initial value again.

16. A heater control apparatus as set forth in claim 14, wherein said heater control variable determining circuit switches the target value from the initial value to the final value after an elapse of a preselected period of time from when the target value reaches the initial value.

17. A heater control apparatus as set forth in claim 14, wherein the initial value is defined within a range of the final value plus 10Ω.

18. A heater control apparatus as set forth in claim 14, wherein the gas concentration sensor works to sense an exhaust gas of an automotive engine.

* * * * *